US007700612B2

(12) United States Patent
Soon-Shiong et al.

(10) Patent No.: US 7,700,612 B2
(45) Date of Patent: Apr. 20, 2010

(54) DI-ESTER PRODRUGS OF CAMPTOTHECIN, PROCESS FOR THEIR PREPARATION AND THEIR THERAPEUTICAL APPLICATIONS

(75) Inventors: Patrick Soon-Shiong, Los Angeles, CA (US); Neil P. Desai, Santa Monica, CA (US); Chunlin Tao, Beverly Hills, CA (US); Cheng Zhi Yu, San Diego, CA (US)

(73) Assignee: Abraxis BioScience, LLC, Los Angeles, CA (US)

( * ) Notice: Subject to any disclaimer, the term of this patent is extended or adjusted under 35 U.S.C. 154(b) by 0 days.

(21) Appl. No.: 10/583,803

(22) PCT Filed: Dec. 23, 2004

(86) PCT No.: PCT/US2004/043719

§ 371 (c)(1),
(2), (4) Date: Jan. 23, 2007

(87) PCT Pub. No.: WO2005/062985

PCT Pub. Date: Jul. 14, 2005

(65) Prior Publication Data

US 2007/0161668 A1 Jul. 12, 2007

Related U.S. Application Data

(60) Provisional application No. 60/532,231, filed on Dec. 23, 2003.

(51) Int. Cl.
*A61K 31/4745* (2006.01)
*C07D 491/22* (2006.01)

(52) U.S. Cl. .......................... 514/283; 546/48
(58) Field of Classification Search ................ 514/283; 546/48
See application file for complete search history.

(56) References Cited

U.S. PATENT DOCUMENTS

| 4,073,943 | A | 2/1978 | Wretlind et al. |
| 4,473,692 | A | 9/1984 | Miyasaka et al. |
| 4,545,880 | A | 10/1985 | Miyasaka et al. |
| 4,604,463 | A | 8/1986 | Miyasaka et al. |
| 4,943,579 | A | 7/1990 | Vishnuvajjala et al. |
| 5,646,159 | A | 7/1997 | Wall et al. |
| 5,731,316 | A | 3/1998 | Cao et al. |
| 5,916,596 | A | 6/1999 | Desai et al. |
| 5,968,943 | A | 10/1999 | Cao et al. |
| 6,040,313 | A | 3/2000 | Wall et al. |
| 6,376,617 | B1 | 4/2002 | Angelucci et al. |
| 6,407,239 | B1 | 6/2002 | Cao et al. |
| 6,492,335 | B1 | 12/2002 | Lerchen et al. |
| 6,506,405 | B1 | 1/2003 | Desai et al. |
| 6,537,579 | B1 | 3/2003 | Desai et al. |

FOREIGN PATENT DOCUMENTS

WO    WO 85/00011 A1    1/1985

OTHER PUBLICATIONS

Wani, M. C. et al.: Plant antitumor agents. J. Org. Chem., vol. 34, pp. 1364-1367, 1969.*
Burke, Thomas G., *Annals of the New York Academy of Sciences*, 803, 29-31 (1996).
Danks et al., *Cancer Research*, 58, 20-22 (Jan. 1, 1998).
Du et al., *Bioorganic & Med. Chem.*, 11, 451-458 (2003).
Giovanella et al., *Cancer Research*, 51, 3052-3055 (Jun. 1, 1991).
Gottlieb et al., *Cancer Chemotherapy Reports*, Part 1, 54(6), 461-470 (Dec. 1970).
Gottlieb et al., *Cancer Chemotherapy Reports*, Part 1, 56(1), 103-105 (Feb. 1972).
Heymann, Eberhard, in *Enzymatic Basis of Detoxication*, vol. II, 291-323, New York: Academic Press, Inc. (1980).
Heymann, Eberhard, in *Metabolic Basis of Detoxication*, 229-245, New York: Academic Press, Inc. (1982).
Hsiang et al., *Cancer Research*, 49, 4385-4389 (Aug. 15, 1989).
Moertel et al., *Cancer Chemotherapy Reports*, Part 1, 56 (1), 95-101 (Feb. 1972).
Muggia et al., *Cancer Chemotherapy Reports*, Part 1, 56 (4), 515-521 (Aug. 1972).
Natelson et al., *Annals of the New York Academy of Sciences*, 803, 224-230 (1996).
Pan et al., *Bioorganic & Med. Chem Lett.*, 13, 3739-3741 (2003).
Potter et al., *Cancer Res.*, 58, 2646-2651 (Jun. 15, 1998).
Strand et al. in *Microspheres: Medical and Biological Applications*, 193-227, Boca Raton FL: CRC Press (1988).
Satoh, Tetsuo in *Reviews in Biochemical Toxicology*, 8, 155-181, New York: Elsevier (1987).
Satoh et al., *Annu. Rev., Pharmacol. Toxicol.*, 38, 257-288 (1998).
Schaeppi et al., *Cancer Chemotherapy Reports*, Part 3, 5(1), 25-36 (Sep. 1974).
Tice et al., *J. Controlled Release*, 2, 343-352 (1985).
Tsuji et al., *J. Pharmacobio-Dyn.*, 14, 341-349 (1991).
Wall et al., *Ann Rev. Pharmacol. Toxicol.*, 17, 117-132 (1977).
Wall et al., *J. American Chem. Soc.*, 88(16), 3888-3890 (Aug. 20, 1966).
Wani et al., *J. Med. Chem.*, 23, 554-560 (1980).
Sandman et al., *Chemistry & Biology*, 6, 541-551 (Aug. 1999).
Garcia-Carbonero et al., Current Perspectives on the Clinical Experience, Pharmacology, and Continued Development of the Camptothecins, Clinical Cancer Research, Mar. 2002, vol. 8 pp. 641-661.
Takimoto et al., Clinical Applications of the Camptothecins, Biochimica et Biophysica Acta, 1998, pp. 107-119.

* cited by examiner

*Primary Examiner*—Charanjit S Aulakh
(74) *Attorney, Agent, or Firm*—Leydig, Voit & Mayer, Ltd.

(57) ABSTRACT

The present invention is related to 10,20-di-O ester derivatives of camptothecin and pharmaceutical formulations thereof. The compounds and pharmaceutical formulations of the present invention possess increased biological life span and bioavailability and reduced toxicity, while maintaining anti-cancer activity.

56 Claims, No Drawings

DI-ESTER PRODRUGS OF CAMPTOTHECIN, PROCESS FOR THEIR PREPARATION AND THEIR THERAPEUTICAL APPLICATIONS

CROSS-REFERENCE TO RELATED PATENT APPLICATIONS

This patent application claims the benefit of U.S. Provisional Patent Application No. 60/532,231, filed Dec. 23, 2003, which is incorporated by reference herein.

FIELD OF THE INVENTION

The present invention relates the derivatives of camptothecin. More particularly, the invention relates to di-ester derivatives of camptothecin, methods of preparing di-ester derivatives of camptothecin and pharmaceutical compositions comprising camptothecin di-ester derivatives.

BACKGROUND OF THE INVENTION

Camptothecin (CPT), shown in formula I:

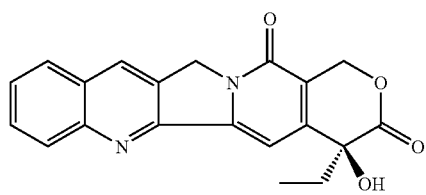

(I)

was isolated and purified by Wall and coworkers in 1966 (*J. Am. Chem. Soc.* 88, 3888, (1966)). This compound was initially tested against the mouse leukemia L 1210 system and found to be active. The compound was quickly tested in human clinical trials. However, the subsequent biological evaluation indicated that this compound is highly toxic and consequently is unusable as a chemotherapeutic agent (Gottlieb et al., *Cancer Chemother. Rep.* 54, 461, (1970), and 56, 103, (1972); Muggia et al., *Cancer Chemother. Rep.* 56, 515, (1972); Moertel et al., *Cancer Chemother. Rep.* 56, 95, (1972); and Schaeppi et al., *Cancer Chemother. Rep.* 5, 25, (1974)). The reason for the failure of the early trial was later found to be due to the selection of an incorrect drug formulation. Camptothecin is insoluble in water. In order to use the drug for intravenous (iv) administration, camptothecin was converted to its sodium form (CPT sodium carboxylate). This form, although water-soluble, is practically devoid of anti-cancer activity. For example, a careful evaluation of these agents in animal models made by Wani et al. revealed that the sodium salt is only 10-20% as potent as the parent camptothecin (*J. Med. Chem.* 23, 554, (1980)). Important parameters for the anticancer activity of camptothecin derivatives have now been established (Wall et al., *Ann. Rev. Pharmacol. Toxicol.* 17, 117, (1977)). The intact lactone form with an α-hydroxyl group with the (S)-configuration at the C-20 position of the molecule is essential for antitumor activity. Maintaining the molecule as an intact lactone is critical for successful treatment.

Camptothecin and camptothecin derivatives are cytotoxic compounds which can be used as chemotherapeutic agents. The cytotoxic activity of camptothecin compounds is believed to arise from the ability of these compounds to inhibit both DNA and RNA synthesis and to cause reversible fragmentation of DNA in mammalian cells. Camptothecin compounds inhibit the enzyme DNA topoisomerase I which is known to relax supercoiled DNA. This relaxation is brought about by breakage of one of the DNA strands in the formation of a covalent topoisomerase I-DNA complex. Camptothecin derivatives are believed to function by reversibly trapping the enzyme-DNA intermediate which is termed the "cleavable complex." (Hsiang et al. *Cancer Research,* 49, 4385, (1989)). The cleavable complex assay developed by Hsiang et al. is a standard test for determining the cytotoxic activity of camptothecin compounds.

Camptothecin and its derivatives have shown a spectacular activity against a wide spectrum of human tumors grown in xenografts in nude mice (Giovanella et al., *Cancer Res.* 51, 3052, (1991), and Natelson et al., *Annals N.Y. Acad. Sci.* 803, 224, (1996)), but much less activity was observed in human clinical trials. This difference in antitumor activity has been associated with the finding that the hydrolysis of lactone to carboxylate of the molecule is much faster in human plasma than in mouse. Burke and coworkers have systematically studied the stability of camptothecin derivatives in human serum (*Annals N.Y. Acad. Sci.* 803, 29, (1996)).

Ten-hydroxycamptothecin (10-HCPT) is a derivative of camptothecin, and also a natural occurring compound. This compound was obtained as an accompanying product on isolation of camptothecin and can now be synthesized from camptothecin in a number of ways. Currently, two anti-cancer agents directly derived from 10-HCPT are commercially available for treatment. One is topotecan, and the other is irinotecan; and their structures are as follows:

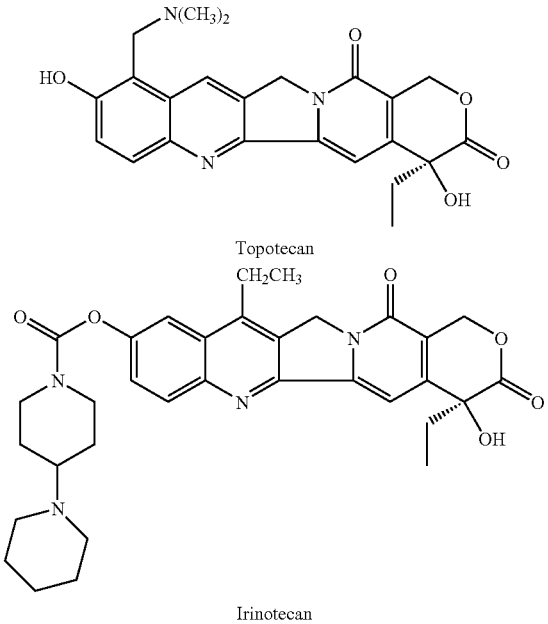

The molecule 10-HCPT, is very potent against cancer cells. Unfortunately, this molecule is not useful for cancer treatment because of its toxicity. The molecule bears two hydroxyl groups, one each at the C-10 and C-20 positions. The C-20 hydroxyl group is adjacent to the carbonyl group of the E-ring of the molecule, which constructs a reactive α-hydroxy lactone moiety. This feature of the molecule makes the lactone moiety very sensitive to hydrolysis, and thus, the molecule is not stable in the body. The 10-phenolic hydroxyl group of 10-HCPT is not stable in the process of enzymatic metabolism reactions. It is well known that phenolic hydroxy-containing moiety of an organic compound can be enzymatically oxidized into a semi-quinone or quinone during the process of metabolism. The corresponding semi-quinone or quinone metabolite is usually more toxic than the parental phenolic compound.

Thus, there is a need for protected 10-HCPT derivatives which are stable in the body and which have a longer biological life span.

Several reports have disclosed the esterification at the C-20 position of camptothecin derivatives. U.S. Pat. Nos. 5,968, 943 and 6,407,239, respectively, disclose the preparation of alkyl and aromatic ester products of camptothecins by introduction of an acyl group at the C-20 position. U.S. Pat. Nos. 6,040,313 and 4,943,579 disclose the esterification of the hydroxyl group at the C-20 position of camptothecin compounds produces a non-toxic water-soluble prodrug. The prodrug is non-toxic even though the parent camptothecin compound itself may be substantially more toxic. Hydrolysis of the ester formed at the C-20 position reforms the parent camptothecin compound after administration, thereby reducing the overall toxicity experienced by the patient during camptothecin therapy.

U.S. Pat. No. 6,492,335 describes the glycoconjugates of camptothecin derivatives in which at least one carbohydrate component is linked via suitable spacers with the 20-hydroxyl group of a camptothecin derivative. U.S. Pat. No. 6,376,617 reported the preparation of water soluble polymeric conjugates of camptothecin with N-(2-hydroxypropyl)methacryloylamide linked via a spacer group to the C-20 position. The conjugates possess enhanced antitumor activity and decreased toxicity with respect to the free drug. U.S. Pat. No. 5,646,159 discloses the esterification of 10,11-dioxymethylenecamptothecin with amino acid derivatives as acylating reagents at the C-20 position to provide several water-soluble compounds. U.S. Pat. No. 5,731,316 discloses the preparation of alkyl or alkenyl ester products of camptothecins by the esterification reaction at the C-20 position.

These patents disclose the single protection of the CPT molecule, meaning that the esterification reaction takes place at the C-20 position. Although 10-HCPT and its derivatives are very potent against cancer cells, they are not very useful due to high toxicities, lack of stability, and shortened biological life spans. Thus, it is very desirable to use the present invention which is able to overcome the problems associated with prior art 10-HCPT and other camptothecin derivatives.

Microparticles and foreign bodies present in the blood are generally cleared from the circulation by the "blood filtering organs", namely the spleen, lungs and liver. The particulate matter contained in normal whole blood comprises red blood cells (typically 8 microns in diameter), white blood cells (typically 6-8 microns in diameter), and platelets (typically 1-3 microns in diameter). The microcirculation in most organs and tissues allows the free passage of these blood cells. When microthrombii (blood clots), with the size greater than 10-15 microns, are present in circulation, a risk of infarction or blockage of the capillaries will be generated, leading to ischemia or oxygen deprivation and possible tissue death. Injection into the circulation of particles greater than 10-15 microns in diameter, therefore, must be avoided. A suspension of particles less than 7-8 microns, is however, relatively safe and has been used for the delivery of pharmacologically active agents in the form of liposomes and emulsions, nutritional agents, and contrast media for imaging applications.

The size of particles and their mode of delivery determine their biological behavior. Strand et al. (in *Microspheres-Biomedical Applications*, ed. A. Rembaum, pp 193-227, CRC Press (1988)) have described the fate of particles to be dependent on their size. Particles in the size range of a few nanometers (nm) to 100 nm enter the lymphatic capillaries following interstitial injection, and phagocytosis may occur within the lymph nodes. After intravenous/intraarterial injection, particles less than about 2 microns will be rapidly cleared from the blood stream by the reticuloendothelial system (RES), also known as the mononuclear phagocyte system (MPS). Particles larger than about 7 microns will, after intravenous injection, be trapped in the lung capillaries. After intraarterial injection, particles are trapped in the first capillary bed reached. Inhaled particles are trapped by the alveolar macrophages.

Intravenous drug delivery permits rapid and direct equilibration with the blood stream which carries the medication to the rest of the body. To avoid the peak serum levels which are achieved within a short time after intravascular injection, administration of drugs carried within stable carriers would allow gradual release of the drugs inside the intravascular compartment following a bolus intravenous injection of the therapeutic nanoparticles.

Injectable controlled-release nanoparticles can provide a pre-programmed duration of action, ranging from days to weeks to months from a single injection. They also can offer several profound advantages over conventionally administered medicaments, including automatic assured patient compliance with the dose regimen, as well as drug targeting to specific tissues or organs (Tice and Gilley, *Journal of Controlled Release* 2, 343-352 (1985)).

Pharmaceuticals that are water-insoluble or poorly water-soluble and sensitive to acid environments in the stomach cannot be conventionally administered (e.g., by intravenous injection or oral administration). The parenteral administration of such pharmaceuticals has been achieved by emulsification of the oil solubilized drug with an aqueous liquid (such as normal saline) in the presence of surfactants or emulsion stabilizers to produce stable microemulsions. These emulsions may be injected intravenously, provided the components of the emulsion are pharmacologically inert. U.S. Pat. No. 4,073,943 describes the administration of water-insoluble pharmacologically active agents dissolved in oils and emulsified with water in the presence of surfactants such as egg phosphatides, pluronics (copolymers of polypropylene glycol and polyethylene glycol), polyglycerol oleate, etc. PCT International Publication No. WO85/00011 describes pharmaceutical microdroplets of an anaesthetic coated with a phospholipid such as dimyristoyl phosphatidylcholine having suitable dimensions for intradermal or intravenous injection.

SUMMARY OF THE INVENTION

The present invention provides novel 10,20-di-ester products of 10-HCPT. In keeping with the present invention, both the C-10 and C-20 positions of 10-HCPT are protected by the introduction of acyl groups into the 10-HCPT, one each at the C-10 and C-20 positions. The compounds of the invention significantly increase the biological life span and bioavailability of 10-HCPT while maintaining the inherent anti-cancer activity of 10-HCPT and lowering the toxicity of 10-HCPT.

According to the present inventions, 10,20-di-ester of 10-HCPT derivatives can be activated in vivo and the parent drug is protected. Conversion of the prodrugs to camptothecin is mediated by a group of enzymes called esterases that are present in the blood of many animals, including humans. Since the prodrugs are rapidly distributed throughout the body within a short period of time after delivery, these prodrugs exist at a very low concentration at the time they undergo enzymatic hydrolysis. This prevents camptothecin from precipitating in the blood stream.

By means of the ester-like linkage of the carrier radicals to the C-20 hydroxyl group, the lactone ring in the camptothecin derivatives, which is important for the action, is stabilized. Compared with the underlying toxophores, they have markedly higher tolerability and tumor selectivity and improved solubility.

The introduction of ester functionality at the C-10 position of CPT derivatives will slowly release the active form of 10-hydroxy CPT, which works as the anticancer reagent.

Thus, the compounds disclosed in this invention significantly increase the biological life span and bioavailability of camptothecins while maintaining the inherent anti-cancer activity and lowering the toxicity of the camptothecins.

The present invention also provides methods to enhance drug bioavailability of the di-ester camptothecin derivatives. The present invention further provides a new method, nanoparticle technology, for the formulation and delivery of such hydrophobic products.

The nanoparticle formulation of this present invention provides new delivery system for the camptothecin derives.

Accordingly, the present invention provides new 10-HCPT analogs, which are active against various different types of tumors. The present invention also provides 10,20-di-O-ester products of 10-HCPT, and which, in some embodiments, are water-soluble derivatives thereof.

The present invention further provides prodrugs of 10-HCPT derivatives. The prodrugs can release the parent active 10-HCPT compounds, believed to be by an enzymatic cleavage of 10,20-di-O-ester, after reaching the targeting organs.

The present invention also provides an improved treatment for certain types of cancers using the di-ester camptothecin derivatives described herein.

Additional objects and advantages of the present invention will be set forth in the detailed description of the preferred embodiments which follows.

DETAILED DESCRIPTION OF THE INVENTION

Conversion of the compounds disclosed by the present invention to the parental 10-HCPT derivatives is mediated by a group of enzymes called esterases. Mammalian carboxylesterases represent a multigene family and are present in a wide variety of organs and tissues of many mammalian species (Satoh, in reviews in *Biochemical Toxicology*, 8:155-81, New York: Elsevier, (1987); Heymann, in *Enzymatic Basis of Detoxication*, 2:291-323, New York: Academic, (1980), and in *Metabolic Basis of Detoxication*, 1:229-45, New York: Academic, (1982)). More information about distribution of carboxylesterases in tissues can be found in a review article written by Satoh et al. (*Annu. Rev. Pharmacol. Toxicol.* 38, 257, (1998)). Carboxylesterases are known to be responsible for the hydrolysis of many exogenous compounds, the consequences of which include both activation of prodrugs and deactivation of drugs. Irinotecan, as discussed above, is a prodrug of 7-ethyl-10-HCPT (SN-38). This compound is converted to SN-38 by carboxylesterases (Danks et al., *Cancer Res.* 58, 20, (1998); Potter et al., *Cancer Res.* 58, 2646, (1998); Tsuji et al., *J. Pharmacobio-Dyn.* 14, 341, (1991)). The compounds having a formula II as disclosed by the present invention are rapidly distributed throughout the body within a short period of time after administration, and the di-esters at the positions of C-10 and C-20 (respectively) are subsequently cleaved to release the active parental compounds by carboxylesterases specifically in organ tissues.

The di-ester compounds of the present invention are active in inhibiting topoisomerase I and yet are non-toxic over a wide active dose range. Those compounds enable one to administer greater amounts of the active camptothecin compound as its non-toxic ester prodrug while avoiding the toxicity of the parent compound. Slow hydrolysis of the ester groups at the C-10 and C-20 positions to yield the free hydroxyl group, results in the slow controlled formation of the parent compound after administration of the di-ester prodrug. The slow formation of the parent compound is less toxic than administration of the corresponding amount of the parent compound initially. That is, the present invention allows one to administer a much larger dose of camptothecin compound as the prodrug than as the corresponding parent camptothecin compound. For example, the present invention allows one to administer a 10 fold greater amount of the ester (which is hydrolyzed to the parent compound) than the parent compound itself. While not being bound to any particular theory, it is believed that the di-ester prodrug is slowly hydrolyzed to the parent camptothecin compound limiting damage to cellular tissues, in particular blood cells. The non-toxicity of the compounds of the present invention is an important improvement over prior art camptothecin compounds.

In accordance with the present invention, there are provided 10-HCPT di-ester derivatives with the general formula II:

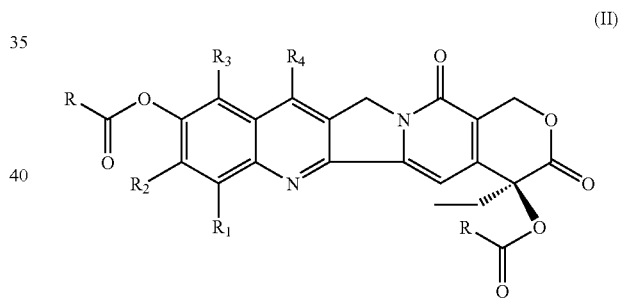

wherein

R is the same or different and R is $C_1$-$C_{30}$ alkyl, $C_2$-$C_{22}$ alkenyl, $C_4$-$C_{20}$ aryl, $(CH_2)_nOR_5$, $(CH_2)_nSR_5$, $(CH_2)_nNR_5R_6$, $(CH_2)_nCOR_7$.

$R_1$, $R_2$, $R_3$, and $R_4$ are the same or different, and are hydrogen, halo, $C_1$-$C_{20}$ alkyl, $C_1$-$C_8$ alkoxyl, $C_4$-$C_{20}$ aryl, and $C_1$-$C_{20}$ silyl.

n is an integer of 1 to 8, $R_5$ and $R_6$, which can be the same or different, are $C_1$-$C_8$ alkyl, $C_2$-$C_6$ alkenyl and $C_4$-$C_{10}$ aryl, $R_7$ is hydroxy, $C_1$-$C_6$ alkoxy, $C_2$-$C_6$ alkenyl, $C_4$-$C_{20}$ aryl or $NR_8R_9$, wherein $R_8$-$R_9$, which can be the same or different, are $C_1$-$C_6$ alkyl.

An illustrative embodiment of the present invention is a compound of formula II, wherein R is the same or different and R is $C_1$-$C_{20}$ alkyl, $C_2$-$C_6$ alkenyl, $C_4$-$C_{20}$ aryl, $(CH_2)_nOR_5$, $(CH_2)_nSR_5$, $(CH_2)_nNR_5R_6$, $(CH_2)_nCOR_7$.

$R_1$, $R_2$, $R_3$, and $R_4$ are the same or different, and are hydrogen, halo, $C_1$-$C_{20}$ alkyl, $C_1$-$C_8$ alkoxyl, $C_4$-$C_{20}$ aryl, and $C_1$-$C_{20}$ silyl, n is an integer of 1 to 8, $R_5$ and $R_6$, which can be the same or different, are $C_1$-$C_8$ alkyl, $C_2$-$C_6$ alkenyl and $C_4$-$C_{10}$ aryl, $R_7$ is hydroxy, $C_1$-$C_6$ alkoxy, $C_2$-$C_6$ alkenyl, $C_4$-$C_{20}$ aryl or $NR_8R_9$, wherein $R_8$-$R_9$, which can be the same or different, are $C_1$-$C_6$ alkyl.

The invention also provides pharmaceutically acceptable salts of the 10-HCPT-di-ester derivatives described above.

The following definitions refer to the various terms used above and throughout the disclosure.

The term "halo" refers to fluoro, chloro, bromo or iodo.

The term "$C_1$-$C_{30}$ alkyl" refers to an alkyl, substituted straight or branched chain alkyl or alkylenyl group, having from 1-30 carbon atoms. In view of availability of alkylating reactants, the alkyl group has preferably 1-22 carbon atoms. Illustrative of the alkyl group include the methyl, ethyl, propyl, isopropyl, butyl, isobutyl, sec-butyl, t-butyl, pentyl, 3-methylbutyl, 2,2-dimethylpropyl, 1,1-dimethylpropyl, hexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, 1-pentylhexyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, 1-hexylnonyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosinyl, tricosinyl, tetracosinyl and pentacosinyl groups.

The term "$C_2$-$C_{22}$ alkenyl" represents an alkenyl group, this has from 2 to 22 carbon atoms, and may be a straight or branched chain group, preferably, natural or unnatural fatty acid. It may have 1 or more, preferably from 2 to 6, double bonds. Examples of such groups include the vinyl, alkyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 1-octenyl, 8-nonenyl, 1-nonenyl, 1-decenyl, 9-decenyl, 8-tridecenyl, cis-8-pentadecenyl, trans-8-pentadecenyl, 8-heptadecenyl, 8-heptadecenyl, 8,11-heptadecadienyl, 8,11,14-heptadecatrienyl, 4,7,11,14-nonadecatetraenyl and 2,6-dimethyl-8-(2,6,6-trimethyl-1-cyclohexen-1-yl)-1,3,5,7-nonatetraen-1-yl, cis-10-nonadecaenyl, 10,13-nonadecadienyl, cis-7,10,13-nonadecatrienyl, 5,8,11,14-nonadecatetraenyl, nonadecapentaenyl, henecosatetraenyl, henecosapentaenyl, henecosahexaenyl, myristyl, and eicosyl groups.

When the alkyl groups are branched, the branched chains may form a cycloalkyl group such as cyclopentyl, cyclohexyl, cycloheptyl, or cyclooctyl group.

The term "$C_1$-$C_8$ alkoxy" refers to an alkoxy group with one to eight carbon alkyl groups, and the alkyl moiety thereof generally corresponds to the $C_1$-$C_{30}$ alkyl groups describes above and can be selected therefrom. Examples of alkoxy groups are those derived from straight or branched chain lower alkyl groups with 1-8 carbon atoms, and include, for example, methoxy, ethoxy n-propoxy, isopropoxy, n-butoxy, isobutoxy, sec-butoxy, tert-butoxy, n-pentyloxy, isopentyloxy, n-hexyloxy, cyclohexoxy, n-heptyloxy, n-octyloxy and 2-ethylhexyloxy.

The term "$C_4$-$C_{20}$ aryl" refers to an aromatic or heteroaromatic ring, including by way of example, phenyl, naphthyl, furanyl imidazolyl and thionyl. The aryl ring can be substituted with substituents selected from the group consisting of halo, $C_1$-$C_6$ alkyl or $C_1$-$C_6$ alkoxy, or alkyl amino. Examples include 4-chlorophenyl, 2-fluorophenyl, 4-fluorophenyl, 3-fluorophenyl, 4-methylphenyl, 4-ditrifluorophenyl, 2-ethylphenyl, 3-n-propylphenyl, 4-isopropyl-phenyl, 4-n-butylphenyl, 4-t-butylphenyl, 4-sec-butylphenyl, 4-dimethylaminophenyl, 3,4-dimethylphenyl, 4-methoxyphenyl, 4-ethoxyphenyl, 4-isopropoxyphenyl, 3-isobutoxyphenyl, 4-t-butoxyphenyl, 4-nitrophenyl, 2-furan, 2-pyridyl, 3-pyridyl, 2-thiophenyl, 3-thiophenyl, 1-naphthyl, 2-naphthyl, 2-indolyl and the like.

The term "$(CH_2)_nOR_5$, $(CH_2)_nSR_5$ and $(CH_2)_nNR_6R_6$" refers to the alkyl groups substituted with oxygen, sulfur and nitrogen, wherein $R_5$ and $R_6$ include hydrogen, or $C_1$-$C_6$ alkyl groups, preferably $C_1$-$C_4$ alkyl groups, $C_2$-$C_6$ alkenyl groups, $C_4$-$C_{10}$ aryl groups, and n is an integer of 1 to 8, preferably, n is the integer 1, 2 or 3. Preferred examples of the alkyl group substituted with oxygen, sulfur or nitrogen include methoxymethyl, ethoxymethyl, propoxymethyl, n-butoxymethyl, 2-methoxyethyl, 2-ethoxyethyl, 2-propoxyethyl, 3-methoxypropyl, 3-ethoxypropyl, 3-propoxypropyl, 4-methoxybutyl, 4-propoxybutyl, dimethoxymethyl, 2,2-dimethoxyethyl, diethoxymethyl, 2,2-diethoxyethyl, dipropoxymethyl and 2,2-dipropoxyethyl groups. Preferred examples of $(CH_2)_nSR_5$ are methylthiomethyl, ethylthiomethyl, propylthiomethyl, n-butylthiomethyl, 2-methylthiolethyl, 2-ethylthiolethyl, 2-propylthiolethyl, 3-methylthiopropyl, 3-ethylthiopropyl, 3-propylthiopropyl, 4-methylthiobutyl, and 4-propylthiobutyl groups. Preferred examples of $(CH_2)_nNR_5R_6$ are aminomethyl, dimethylaminomethyl, (N-acetyl) methylaminomethyl, diethylaminomethyl, dipropylaminomethyl, dibutylaminomethyl, dimethylaminoethyl, diethylaminoethyl, dipropylaminoethyl, and dibutylaminoethyl groups.

The term "$(CH_2)_nCOR_7$" refers to carboxylic acid, ester, or amide, wherein n is an integer of 1 to 8, preferably n is an integer 1, 2, 3 or 4, and $R_7$ is hydroxy, $C_1$-$C_6$ alkoxy or $NR_9R_9$. When $R_7$ is $NR_8R_9$, $R_8$ and $R_9$ can be the same or different and are alkyl or substituted alkyl groups with one to six carbon atoms. The alkyl moiety of $R_8$ and/or $R_9$ generally correspond to the $C_1$-$C_{20}$ alkyl groups discussed above and can be selected therefrom. Preferred examples of the alkylamino group are those derived from hydrogen, and straight or branched chain lower alkyl groups with 1-6 carbon atoms, such as methyl, ethyl, propyl, butyl, pentyl and hexyl groups.

The term "$C_3$-$C_{20}$ silyl" refers to an $Si(R_{10}R_{11}R_{12})$, wherein $R_{10}$, $R_{11}$, $R_{12}$ can be the same or different and are the substituted straight or branched chain alkyl or alkenyl groups and generally has 3-20 carbon atoms. The alkyl moiety thereof generally corresponds to the aforesaid alkyl group. Preferred illustrative examples are trimethylsilyl, triethylsilyl, tributylsilyl, t-butyldimethylsilyl, t-butyldiethylsilyl and t-butyldiphenylsilyl.

In the above general formula (II), either one of the substituents $R_1$ and $R_2$ is preferably hydrogen. The radical $R_3$ located in the C-9 position is preferably a halogen atom, nitro or an alkyl group of 1-10 carbon atoms, with a substitution, such as chloro, amino, or alkylamino groups being preferred. The alkyl moiety is preferably a lower alkyl or substituted alkyl group with 1-8 carbon atoms. The alkyl moiety thereof generally corresponds to the $C_1$-$C_{20}$ alkyl group discussed above. Illustrative of the substituted alkyl groups are, for example, aminomethyl, aminoethyl, aminopropyl, dimethylaminomethyl, dimethylaminoethyl, dimethylaminopropyl, diethylaminomethy, diethylaminoethyl, diethylaminopropyl. The alkylamino groups are, for example, methylamino, ethylamino, propylamino, isopropylamino, n-butylamino, tert-butylamino, pentylamino, hexylamino, heptylamino and octylamino groups.

In the above general formula (II), $R_4$ located in the C-7 position represents halo, phenyl, an alkyl group or a $Si(R_{10}R_{11}R_{12})$, group. Preferably, $R_4$ is hydrogen, a halogen atom or an alkylsilyl, with the alkylsilyl group being most preferable, such as trimethylsilyl, t-butyldimethylsilyl, triethylsilyl, and t-butyldiphenylsilyl. In case of $R_4$ being a substituted or unsubstituted phenyl group, preferable examples of the phenyl-substituted alkyl group include phenoxymethyl, p-methylphenoxymethyl, o-chlorophenoxymethyl, 2-phenoxyethyl, 3-phenoxypropyl and 4-phenoxybutyl group.

In the above general formula (II), R is preferably an unsubstituted or substituted alkyl group, aromatic group, or heteroaromatic group. The most preferable substituents on the aromatic or heteroaromatic ring are hydrogen, halogen, $C_1$-$C_4$ alkyl, $NR_8R_9$ and the like. More preferably, the substituted alkyl groups are $(CH_2)_nOR_5$, $(CH_2)_nSR_5$, $(CH_2)_nNR_5R_6$ wherein n is either 1 or 2, and $(CH_2)_nCOR_7$ wherein n is 1, 2, 3 or 4, and $R_5$ to $R_9$, which can be the same or different, are the same as described above. Illustrative examples of the preferred R groups are aminomethyl, dimethylaminomethyl, methoxymethyl, methoxyethyl, methoxyethyl, ethyl, propyl, hexyl, phenyl, 4-chlorophenyl, 2-fluorophenyl, 4-fluorophenyl, 3-fluorophenyl, 4-methylphenyl, 4-ditrifluorophenyl, 3,4-dimethylphenyl, 4-methoxyphenyl, 4-ethoxyphenyl, 4-isopropoxyphenyl, 4-nitrophenyl, 2-furan, 3-pyridyl, 2-thiophenyl and the like. The most preferable di-esters of 10-HCPT in accordance with the invention are methoxylacetate, ethoxylacetate, propoxylacetate, glycinate, methylaminoacetate, dimethylaminoacetate, diethylaminoacetate, benzoate, fluorobenzoate, methoxy benzoate, succinate, and glutate.

According to the present invention, any camptothecin compounds having available hydroxyl groups at the C-10 and C-20 positions may be used to prepare the di-ester derivatives. Suitable camptothecin compounds are described, for example, in U.S. Pat. No. 4,545,880, U.S. Pat. No. 4,604,463, and U.S. Pat. No. 4,473,692. These patents are incorporated herein by reference for a more complete description of camptothecin compounds which can be used to prepare the di-esters of the present invention.

Camptothecin compounds having the following general structure as depicted by the general formula III:

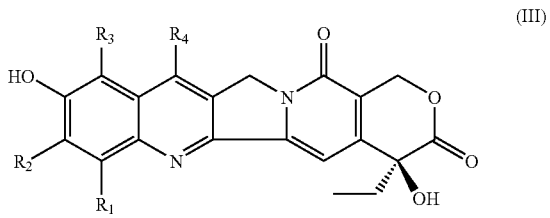

(III)

can be converted to the di-ester camptothecin derivatives of the present invention.

In the camptothecin compounds of formula III, the substituents $R_1$, $R_2$, $R_3$, and $R_4$ are not critical and can be any of a wide variety of groups and combinations of groups, such as H, and unsubstituted and substituted alkyl, alkenyl, alkoxy, silyl, aryl, and alkylsilyl groups, and the like. Preferably, $R_1$, $R_2$, $R_3$, and $R_4$ generally correspond to $R_1$, $R_2$, $R_3$, and $R_4$ of the compounds of the invention, formula II, as described above.

Illustrative examples of the preferred 10-HCPT derivatives that are useful starting materials to form the compounds of the present invention are, 10-hydroxycamptothecin (10-hydroxy-CPT; "camptothecin" is referred to hereinafter simply as "CPT"), 10-hydroxy-7-methyl-CPT, 10-hydroxy-7-ethyl-CPT, 10-hydroxy-7-propyl-CPT, 10-hydroxy-7-benzyl-CPT, 10-hydroxy-7-trimethylsilyl-CPT, 10-hydroxy-7-triethylsilyl-CPT, 10-hydroxy-7-dimethylbutylsilyl-CPT, 10-hydroxy-7-triethylsilyl-CPT, 10-hydroxy-9-nitro-CPT, 10-hydroxy-9-dimethylamino-CPT, 10-hydroxy-9-diethylamino-CPT. The most preferable analogs, as starting materials for the present invention, are 10-HCPT, 7-ethyl-10-HCPT and 7-tert-butyldimethylsilyl-10-HCPT and 9-dimethylamino-10-HCPT.

In accordance with the present invention, there is also provided the processes for the preparation of various 10-HCPT di-ester derivatives of the general formula (II).

The compounds of the present invention are prepared by esterifying the 10,20-position hydroxyl groups of a camptothecin compound to generate the desired product.

Generally, the reaction of 10-HCPT derivatives with the corresponding acylating reagents forms the di-ester products. The preparation of compounds of formula (II) follows the general synthetic procedures that are known in the literature.

The di-ester can be prepared from the corresponding anhydride in the presence of a catalytic amount of acid at elevated temperature. For example, 10-HCPT, 3 to 50 molar equivalent of the acylating reagent with the general formula R'CO—O—COR', and a catalytic amount of concentrated $H_2SO_4$ was added to a round-bottomed flask equipped with a magnetic stirrer. The mixture was stirred at elevated temperature (100±10° C.) under nitrogen gas for 12-48 hours. After cooling to room temperature, the mixture was poured into petroleum ether portion by portion while stirring, and the precipitates were collected by filtration and then dissolved into dichloromethane/water. The separated organic layer was washed with 5% $NaHCO_3$, brine, dried over sodium sulfate, and concentrated. The residue was purified by flash silica gel chromatography eluted with tetrahydrofuran/dichloromethane to afford the desired product in the yield of 10 to 90%.

In this way, any anhydrides can be used for the invention to obtain the desired di-ester product, such as aliphatic, aromatic carboxylic, and heterocyclic carboxylic anhydride. Generally, the anhydride can be prepared from the corresponding acid with the general synthetic method in the prior art.

The di-ester prodrugs of the present invention are also prepared by esterifying the 10,20-hydroxyl groups of camptothecins with the corresponding alkyl or aromatic carboxylic acids. The reaction can be carried out in anhydrous solvent (such as dimethylformamide and methyl sulfoxide) in the presence of one equivalent of dicyclohexylcarbodiimide (DCC) and a catalytic amount of an amine base, preferably a secondary or tertiary amine. Any precipitate which form is removed by filtration and the product is isolated after removal of the solvent. The desired product can be purified with column chromatography. Thus, for example, 7-ethyl-10-HCPT may be allowed to react in methyl sulfoxide with a molar excess, for example up to five-fold molar excess or more, especially 2 mol equivalents, of an acid in anhydrous dimethylformamide in the presence of DCC and 4-dimethylaminopyridine, to afford the desired di-ester product.

Any acid can be used for the invention to obtain the desired di-ester product, including, for example, aliphatic acids, aromatic carboxylic acids, heterocyclic carboxylic acids, and aralkylcarboxylic acids. These acids may contain one or more unsaturated bonds in the molecule and carry one or more substituents such as halogen atoms, amino groups and hydroxyl groups, such as various kinds of amino acids. The illustrative examples are chloroacetic acid, propionic acid, butyric acid, phenylacetic acid, succinic acid, glutaric acid, adipic acid, glycine, alanine, valine, leucine, isoleucine, phenylalanine, tyrosine, tryptophan, leucine, arginine, histidine, aspartate, glutamate, asparagine, glutamine, cysteine, methionine and their derivatives.

The amino or alkylamino groups of di-esters can be converted to an acid addition salt by the addition of a pharmaceutically acceptable acid. Suitable acids include both inorganic and organic acids. Suitable addition salts include, but are not limited to hydrochloride, sulfate, phosphate, diphosphate, hydrobromide, nitrate, acetate, malate, maleate, fumarate, tartrate, succinate, citrate, lactate, methanesulfonate, p-toluenesulfonate, palmoate, salicylate and stearate salts. The salts can be purified by crystallization from a suitable solvent, or dissolved in water and lyophilized.

The compounds disclosed in the present invention are prodrugs of 10-HCPT derivatives. 10-HCPT di-ester derivatives are very active against cancers, but very toxic as well. The compounds of the present invention do not only exhibit the anti-cancer activity of the 10-HCPT derivatives, but they also greatly decrease the toxicity of their parental compound. Thus, the compounds of the present invention can be very effective in the treatment of cancers, including, but not limited to, human cancers of the lung, breast, colon, prostate, melanoma, pancreas, stomach, liver, brain, kidney, uterus, cervix, ovaries urinary track, gastrointestinal, and other solid tumors which grow in an anatomical site. Other solid tumors include, but not limited to, colon and rectal cancers. The compounds of the present invention are also effective in the treatment of the other types of tumors growing in the blood stream and blood borne such as leukemia.

The di-ester of 10-HCPT of the present invention can be administered as a pharmaceutical composition containing the compounds and a pharmaceutically acceptable carrier or diluent. The active materials can also be mixed with other active materials which do not impair the desired action and/or supplement the desired action. The active materials according to the present invention can be administered by any acceptable route including, but not limited to, orally, parenterally, intravenously, intradermally, subcutaneously, through an inhaler or topically, in liquid or solid form.

Oral compositions will generally include an inert diluent or an edible carrier. They can be enclosed in gelatin capsules or compressed into tablets. For the purpose of oral therapeutic administration, the aforesaid compounds can be incorporated with excipients and used in the form of tablets, troches, capsules, elixirs, suspensions, syrups, wafers, chewing gums and the like.

The tablets, pills, capsules and the like can contain the following ingredients: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring may be added. When the dosage unit form is a capsule, it can contain, in addition to material of the above type, a liquid carrier such as a fatty oil. Other dosage unit forms may contain other various materials which modify the physical form of the dosage unit, for example, as coatings. Thus, tablets or pills can be coated with sugar, shellac, or other enteric coating agents. A syrup can contain, in addition to the active compounds, sucrose as a sweetening agent and certain preservatives, dyes and colorings and flavors. Materials used in preparing these various compositions should be pharmaceutically or veterinarally pure and non-toxic in the amounts used.

For the purposes of parenteral therapeutic administration, the active ingredient can be incorporated into a solution or suspension. The solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil, liquid acid, lower alkanols, oils such as corn oil, peanut oil, sesame oil and the like, with emulsifiers such as mono- or di-glyceride of a fatty acid, or a phosphatide, e.g., lecithin, and the like, glycols, polyalkylene glycols, aqueous media in the presence of a suspending agent, for example, sodium carboxymethylcellulose, sodium alginate, poly(vinylpyrrolidone), and the like, alone, or with suitable dispensing agents such as lecithin, polyoxyethylene stearate, and the like. The carrier can also contain adjuvants such as preserving stabilizing, wetting, emulsifying agents and the like together with the penetration enhancer. In all cases the final form, as noted, must be sterile and must also be able to pass readily through an injection device such as a hollow needle. The proper viscosity can be achieved and maintained by the proper choice of solvents or excipients. Moreover, the use of molecular or particulate coatings such as lecithin, the proper selection of particle size in dispersions, or the use of materials with surfactant properties may be utilized.

In accordance with the present invention, there are provided compositions of camptothecin derivatives and methods useful for the in vivo delivery of di-ester of 10-HCPT derivatives in the form of nanoparticles, which are suitable for any route administrations.

U.S. Pat. Nos. 5,916,596, 6,506,405 and 6,537,579 teach the preparation of nanoparticles from the biocompatible polymers, such as albumin. Thus, in accordance with the present invention, there are provided methods for the formation of nanoparticles of present invention by a solvent evaporation technique from an oil-in-water emulsion prepared under conditions of high shear forces (e.g., sonication, high pressure homogenization, or the like).

Thus, in accordance with the present invention, di-ester derivatives of 10-HCPT are dissolved in a water miscible organic solvent (e.g., a solvent having greater than about 10% solubility in water, such as, for example, ethanol) is added to the oil phase at a final concentration in the range of about 1-99% (v/v), more preferably in the range of about 5-25% (v/v) of the total organic phase. The water miscible organic solvent can be selected from such solvents as ethyl acetate, ethanol, tetrahydrofuran, dioxane, acetonitrile, acetone, dimethyl sulfoxide, dimethyl formamide, methylpyrrolidinone, and the like. Alternatively, the mixture of water immiscible solvent with the water miscible solvent is prepared first, followed by dissolution of the pharmaceutically active agent in the mixture.

Next, a protein (e.g., human serum albumin) is added (into the aqueous phase) to act as a stabilizing agent for the formation of stable nanodroplets. Protein is added at a concentration in the range of about 0.05 to 25% (w/v), more preferably in the range of about 0.5-5% (w/v). Unlike conventional methods for nanoparticle formation, no surfactant (e.g. sodium lauryl sulfate, lecithin, Tween® 80, Pluronic® F-68 and the like) is added to the mixture. Optionally, a sufficient amount of the first organic solvent (e.g., chloroform) is dissolved in the aqueous phase to bring it close to the saturation concentration. A separate, measured amount of the organic phase (which now contains the pharmacologically active agent, the first organic solvent and the second organic solvent) is added to the saturated aqueous phase, so that the phase fraction of the organic phase is between about 0.5-15% (v/v), and more preferably between 1% and 8% (v/v).

An emulsion is formed by homogenization under high pressure and high shear forces. Such homogenization is conveniently carried out in a high-pressure homogenizer, typically operated at pressures in the range of about 3,000 up to 30,000 psi. Preferably, such processes are carried out at pressures in the range of about 6,000 up to 25,000 psi. The resulting emulsion comprises very small nanodroplets of the nonaqueous solvent (containing the dissolved pharmacologically active agent) and very small nanodroplets of the protein-stabilizing agent. Acceptable methods of homogenization include processes imparting high shear and cavitation such as high pressure homogenization, high shear mixers, sonication, high shear impellers, and the like.

Finally, the solvent is evaporated under reduced pressure to yield a colloidal system composed of protein-coated nanoparticles of pharmacologically active di-ester of 10-HCPT and protein. Acceptable methods of evaporation include the use of rotary evaporators, falling film evaporators, spray driers, freeze driers, and the like. Thus, a colloidal dispersion system (pharmacologically active agent and protein) in the form of extremely small nanoparticles (i.e., particles in the range of about 10-200 nm diameter) can be sterile-filtered. The preferred size range of the particles is between about 50-170 nm, depending on the formulation and operational parameters.

Colloidal systems prepared in accordance with the present invention can be further converted into powder form by removal of the water, e.g., by lyophilization at a suitable temperature-time profile. The protein (e.g., human serum albumin) itself acts as a cryoprotectant, and the powder is easily reconstituted by addition of water, saline or buffer, without the need to use such conventional cryoprotectants as mannitol, sucrose, glycine, and the like. While not required, it is of course understood that conventional cryoprotectants can be added to invention formulations if so desired.

The polymeric shell containing solid or liquid cores of pharmacologically active agent allows for the delivery of high doses of the pharmacologically active agent in relatively small volumes. This minimizes patient discomfort at receiving large volumes of fluid and minimizes hospital stay. In addition, the walls of the polymeric shell or coating are generally completely degradable in vivo by proteolytic enzymes (e.g., when the polymer is a protein), resulting in no side effects from the delivery system as is the case with current formulations.

A number of biocompatible materials can be employed in the practice of the present invention for the formation of a polymeric shell. As used herein, the term "biocompatible" describes a substance that does not appreciably alter or affect in any adverse way, the biological system into which it is introduced. Several biocompatible materials may be employed in the practice of the present invention for the formation of a polymeric shell. For example, naturally occurring biocompatible materials such as proteins, polypeptides, oligopeptides, polynucleotides, polysaccharides (e.g., starch, cellulose, dextrans, alginates, chitosan, pectin, hyaluronic acid, and the like), lipids, and so on, are candidates for such modification.

As examples of suitable biocompatible materials, naturally occurring or synthetic proteins may be employed. Examples of suitable proteins include albumin, insulin, hemoglobin, lysozyme, immunoglobulins, $\alpha$-2-macroglobulin, fibronectin, vitronectin, fibrinogen, casein and the like, as well as combinations of any two or more thereof. Similarly, synthetic polymers are also good candidates for preparation of the drug formulation. Examples include polyalkylene glycols (e.g., linear or branched chain), polyvinyl alcohol, polyacrylates, polyhydroxyethyl methacrylate, polyacrylic acid, polyethyloxazoline, polyacrylamides, polyisopropyl acrylamides, polyvinyl pyrrolidinone, polylactide/glycolide and the like, and combinations thereof, are good candidates for the biocompatible polymer in the invention formulation.

These biocompatible materials can also be employed in several physical forms such as gels, crosslinked or uncrosslinked to provide matrices from which the pharmacologically active ingredient, for example paclitaxel, can be released by diffusion and/or degradation of the matrix. Temperature sensitive materials can also be utilized as the dispersing matrix for the invention formulation. Thus for example, the camptothecin di-ester may be injected in a liquid formulation of the temperature sensitive material (e.g., copolymers of polyacrylamides or copolymers of polyalkylene glycols and polylactide/glycolides) which gel at the tumor site and provide slow release of di-ester of 10-HCPT.

Particles of biologic substantially completely contained within a polymeric shell, or associated therewith, prepared as described herein, are delivered neat, or optionally as a suspension in a biocompatible medium. This medium may be selected from water, buffered aqueous media, saline, buffered saline, optionally buffered solutions of amino acids, optionally buffered solutions of proteins, optionally buffered solutions of sugars, optionally buffered solutions of carbohydrates, optionally buffered solutions of vitamins, optionally buffered solutions of synthetic polymers, lipid-containing emulsions, and the like.

In addition, the polymeric shell optionally can be modified by a suitable agent, wherein the agent is associated with the polymeric shell through an optional covalent bond. Covalent bonds contemplated for such linkages include ester, ether, urethane, di-ester, amide, secondary or tertiary amine, phosphate ester, sulfate ester, and the like bonds. Suitable agents contemplated for this optional modification of the polymeric shell include synthetic polymers (polyalkylene glycols (e.g., linear or branched chain polyethylene glycol), polyvinyl alcohol, polyhydroxyethyl methacrylate, polyacrylic acid, polyethyloxazoline, polyacrylamide, polyvinyl pyrrolidinone, and the like), phospholipids (such as phosphatidyl choline (PC), phosphatidyl ethanolamine (PE), phosphatidyl inositol (PI), sphingomyelin, and the like), proteins (such as enzymes, antibodies, and the like), polysaccharides (such as starch, cellulose, dextrans, alginates, chitosan, pectin, hyaluronic acid, and the like), chemical modifying agents (such as pyridoxal 5'-phosphate, derivatives of pyridoxal, dialdehydes, diaspirin esters, and the like), or combinations of any two or more thereof.

The prepared nanoparticle with this invention can be administered by any acceptable route including, but not limited to, orally, intramuscularly, transdermally, intravenously, through an inhaler or other air borne delivery systems, and the like. When preparing the composition for injection, particularly for intravenous delivery, the continuous phase preferably comprises an aqueous solution of tonicity modifiers, buffered to a pH below 7, more preferably below 6.

The prepared nanoparticles of this invention can be enclosed in a hard or soft capsule, can be compressed into tablets, or can be incorporated with beverages, food or otherwise into the diet. Capsules can be formulated by mixing the nanoparticle with a pharmaceutical diluent which is inert and inserting this mixture into a hard gelatin capsule having the appropriate size. If soft capsules are desired, a slurry of the compound with an acceptable vegetable, light petroleum, or other inert oil can be encapsulated by machine into a gelatin capsule. The percentage of the final composition and the preparations may, of course, be varied and may conveniently range between 1 and 90% of the weight of the final form, e.g., tablet. The amount in such therapeutically useful compositions is such that a suitable dosage will be obtained. Preferred compositions according to the current invention are prepared so that an oral dosage unit form contains between about 5 to about 50% by weight (% w) in dosage units weighing between 50 and 1000 mg.

In addition, the compounds and the formulations of the present invention can be used in combination with other drugs and formulations for the treatment of cancers such as Taxol®, Taxotere®, or their derivatives, VP-16, 5-FU, as well as cisplatin and derivatives thereof.

Another important feature of the method provided by the present invention relates to the relatively low apparent overall toxicity of the 10-HCPT derivatives administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity.

Other features of the present invention will become apparent in view of the following examples, which are given for illustration of the invention and are not intended to be limiting thereof.

EXAMPLE 1

This example illustrates the preparation of camptothecin 10,20-di-O-butyrate (CY1). To a round-bottomed flask was added 10-hydroxycamptothecin (3.0 g, 8.24 mmol), butyric anhydride (60 mL), followed by adding concentrated sulfuric acid (10 drops) dropwise at room temperature. The obtained mixture was stirred at about 100° C. for overnight. After cooling to room temperature, the mixture was poured into 350 mL petroleum ether portion by portion while stirring. After stirring for about 1 h, the crude product precipitated was collected by filtration. The crude product was then dissolved into $DCM/H_2O$. The organic layer was washed with 5% $NaHCO_3$, brine, dried ($MgSO_4$) and concentrated. The residue was purified by flash silica gel chromatography eluted with THF/DCM (3-5%) to afford the white solid (3.7 g, 89%). Anal. Calcd for $(C_{28}H_{28}N_2O_7+H)^+$ and $(C_{28}H_{28}N_2O_7+Na)^+$: 505 and 527. Found: 505 and 527.

EXAMPLE 2

This example illustrates the preparation of camptothecin 10,20-di-O-isobutyrate (CY2). To a round-bottomed flask was added 10-hydroxycamptothecin (1.2 g, 3.29 mmol), isobutyric anhydride (40 mL), and followed by adding concentrated sulfuric acid (8 drops) dropwise at room temperature. The reaction mixture was stirred at 100° C. for 16 h. After cooling to room temperature, the mixture was poured into 250 mL petroleum ether portion by portion while stirring. After stirring for about 45 min, the crude product precipitated was collected by vacuum filtration. The crude product was partitioned with DCM (200 mL) and 5% $NaHCO_3$ (80 mL), brine. The organic layer was washed with brine (1×100 mL) and dried over anhydrous $MgSO_4$, filtered and concentrated in vacuo. The residue was purified by flash silica gel column chromatography (THF in DCM, 3-5%) to afford a white solid (1.59 g, 96%). Anal. Calcd for $(C_{28}H_{28}N_2O_7+H)^+$ and $(C_{28}H_{28}N_2O_7+Na)^+$: 505 and 527. Found: 505 and 527.

EXAMPLE 3

This example illustrates the preparation of camptothecin 10,20-di-O-hexonate (CY4). To a round-bottomed flask was added 10-hydroxycamptothecin (1.8 g, 4.94 mmol), hexanoic anhydride (50 mL), and followed by adding concentrated sulfuric acid (9 drops) dropwise at room temperature. The reaction mixture was stirred at 100° C. for 17 h. After cooling to room temperature, the mixture was poured into 300 mL petroleum ether portion by portion while stirring. After stirring for about 1 h, the crude product precipitated was collected by vacuum filtration. The crude product was partitioned with DCM (250 mL) and 5% $NaHCO_3$ (80 mL), brine. The organic layer was washed with brine (1×100 mL) and dried over anhydrous $MgSO_4$, filtered and concentrated in vacuo. The residue was purified by flash silica gel column chromatography (THF in DCM, 5-10%) to afford a white solid (2.38 g, 86%). Anal. Calcd for $(C_{32}H_{36}N_2O_7+H)^+$ and $(C_{32}H_{36}N_2O_7+Na)^+$: 561 and 583. Found: 561 and 583.

EXAMPLE 4

This example illustrates the preparation of camptothecin 10,20-di-O-tert-butylaminoacetate (CY28). To a three neck flask was added 10-hydroxycamptothecin (1.8 g, 4.89 mmol), BOC-glycine (3.9 g, 22 mmol) and DMF (40 mL), at 0° C. DMAP (548 mg, 4.89 mmol) and DCC (5.0 g, 24.45 mmol) were added sequentially to the reaction mixture. After the addition, the reaction mixture was stirred at room temperature for 72 h. Cooled hexane (150 mL) was added to the brownish mixture while stirring. After one hour, the mixture was filtered. The residue was coevaporated with toluene once and purified by flash silica gel column chromatography (THF:DCM, 1:10) to afford a yellow solid (238.1 mg, 7.2%). $^1$H NMR (CDCl$_3$, 500 MHz): δ 8.34 (s, 1H), 8.25 (d, J=7.4 Hz, 1H), 8.01 (s, 1H), 7.71 (d, J=2.1 Hz, 1H), 7.57 (dd, J=7.4, 2.0 Hz, 1H), 5.54 (AB, Δγ=116.5 Hz, J=13.8 Hz, 2H), 5.27 (d, J=1.7 Hz, 2H), 5.25 (t, J=4.7 Hz, 1H), 4.99 (t, J=5.2 Hz, 1H), 4.79 (s, 2H), 4.54 (d, J=4.3 Hz, 2H), 2.28-2.13 (m, 2H), 1.58 (s, 9H), 1.46 (s, 9H), 0.99 (t, J=5.9 Hz, 3H). ESI-MS: calcd. for C$_{34}$H$_{39}$N$_4$O$_1$Na (M+Na+H)$^+$: 702. Found: 702.

EXAMPLE 5

This example illustrates the preparation of camptothecin 10,20-di-O-methoxyacetate (CY30). To a three neck flask was added 10-hydroxycamptothecin (424 mg, 1.16 mmol), methoxyacetic acid (356 μL, 4.64 mmol) and DMF (40 mL), at 0° C. DMAP (130 mg, 1.16 mmol) and DCC (1.2 g, 5.8 mmol) were added sequentially to the reaction mixture. After the addition, the reaction mixture was stirred at room temperature for 48 h. Cooled hexane (100 mL) was added to the brownish mixture while stirring. After one hour, the mixture was filtered. The residue was coevaporated with toluene once and purified by flash silica gel column chromatography (THF:DCM, 1:7) to afford a yellow solid. $^1$H NMR (CDCl$_3$, 500 MHz): δ 8.34 (s, 1H), 8.23 (d, J=7.2 Hz, 1H), 7.76 (d, J=2.2 Hz, 1H), 7.61 (dd, J=7.2, 2.0 Hz, 1H), 7.20 (s, 1H), 5.58 (AB, Δγ=120 Hz, J=14.2 Hz, 2H), 5.30 (s, 2H), 4.39 (s, 2H), 4.23 (dd, J=23.3, 13.5 Hz, 2H), 3.59 (s, 3H), 3.46 (s, 3H), 2.28-2.13 (m, 2H), 0.99 (t, J=6.0 Hz, 3H). ESI-MS: calcd. for C$_{26}$H$_{24}$N$_2$O$_9$Na (M+Na)$^+$: 531. Found: 531.

EXAMPLE 6

This example illustrates the preparation of camptothecin 10,20-di-O-aminoacetate (CY32). To a solution of camptothecin 10,20-di-O-tert-butylaminoacetate (40 mg, 0.06 mmol) in MeOH (3 mL) at 0° C. was added saturated solution of HCl in dioxane (0.5 mL) within 5 min. After addition, the reaction mixture was warmed up to rt and stood for 2 h. The reaction mixture was stored at 4° C. overnight. TLC showed the complete disappearance of starting material. The reaction mixture was washed with chloroform (3×5 mL) and subjected to lyophilization to afford the desired product as a yellow foam (12.7 mg, 38.5%). $^1$H NMR (CDCl$_3$, 500 MHz): δ 7.94 (s, 1H), 7.76 (d, J=9.2 Hz, 1H), 7.25 (dd, J=9.5, 2.6 Hz, 1H), 7.18 (s, 1H), 6.92 (d, J=2.5 Hz, 1H), 5.57 (AB, Δγ=86 Hz, J=16.3 Hz, 2H), 4.35 (d, J=4.8 Hz, 2H), 4.01 (s, 2H), 3.88 (s, 2H), 2.36-2.26 (m, 2H), 1.10 (t, J=7.3 Hz, 3H).

EXAMPLE 7

This example illustrates the preparation of Camptothecin 10,20-di-O-benzoate (CY55). To a solution of 10-hydroxy camptothecin (605 mg, 1.66 mmol) in pyridine (50 mL) at 0° C. was added benzoic anhydride (2.25 g, 996 mmol). The reaction mixture was stirred at room temperature for 24 h and concentrated on rotavapor to remove most of the pyridine. Cold hexanes (100 mL) was added to the residue. The suspension was stored at 0° C. for 2 days and filtered. The solid was collected and purified by flash silica gel column chromatography (THF:DCM, 1:20) to afford a yellow solid (647 mg, 68.1%). $^1$H NMR (CDCl$_3$, 500 MHz): δ 8.36 (s, 1H), 8.25-8.23 (m, 2H), 8.20 (d, J=7.4 Hz, 1H), 7.81 (d, J=2.5 Hz, 1H), 7.70-7.61 (m, 3H), 7.56-7.48 (m, 4H), 5.77 (d, J=17.2 Hz, 1H), 5.47 (d, J=17.1 Hz, 1H), 5.34-5.25 (m, 2H), 2.48-2.43 (m, 1H), 2.36-2.27 (m, 1H), 1.68 (brs, 1H), 1.10 (t, J=7.5 Hz, 3H). ESI-MS: calcd. for C$_{34}$H$_{25}$N$_2$O$_7$ (M+H)$^+$: 573. Found: 573.

EXAMPLE 8

This example illustrates the preparation of 7-ethylcamptothecin 10,20-di-O-benzoate (CY57). To a round-bottomed flask was added SN-38 (480 mg, 1.22 mmol), propionic anhydride (50 mL), followed by adding concentrated sulfuric acid (14 drops) dropwise at room temperature. The obtained mixture was stirred at about 100° C. for 17 h. After cooling to room temperature, the mixture was poured into 350 mL petroleum ether portion by portion while stirring. After stirring for about 1 hr and standing at 0° C. for 48 h, the crude product was collected by filtration. The crude product was then dissolved into DCM/H$_2$O. The organic layer was washed with 5% NaHCO$_3$, brine, dried (MgSO$_4$) and concentrated. The residue was purified by flash silica gel chromatography eluted with THF/DCM (2-5%) to afford the white solid (268 mg, 44%). $^1$H NMR (CDCl$_3$, 500 MHz): δ ESI-MS: calcd. for C$_{28}$H$_{29}$N$_2$O$_7$ (M+H)$^+$: 505. Found: 505.

EXAMPLE 9

This example illustrates the preparation of 7-ethylcamptothecin 10,20-di-O-hexanoate (CY189). To a solution of SN38 (1.62 g, 4.1 mmol) in pyridine (125 mL) at 0° C. was added hexanoic anhydride (5.7 mL, 24.2 mmol). The reaction mixture was stirred at room temperature for 21 h and quenched by 20 mL of methanol. The mixture was stirred for additional 2 h at room temperature and concentrated on rotavapor to dryness. The residue was purified by flash silica gel column chromatography (THF:DCM, 1:30) to afford a pale yellow solid (2.33 g, 96%). $^1$H NMR (CDCl$_3$, 500 MHz): δ 8.20 (d, J=9.2 Hz, 1H), 7.84 (s, 1H), 7.56 (d, J=9.2 Hz, 1H), 7.17 (s, 1H), 5.68 (d, J=17.1 Hz, 1H), 5.41 (d, J=17.1 Hz, 1H), 5.24 (d, J=3.8 Hz, 2H), 3.15 (dd, J=15.2, 7.8 Hz, 2H), 2.66 (t, J=7.5 Hz, 2H), 2.35 (t, J=7.5 Hz, 4H, methylene), 1.66-1.25 (m, 15H), 0.97 (t, J=6.8 Hz, 3H), 0.89-0.85 (m, 6H). ESI-MS: calcd. for C$_{34}$H$_{41}$N$_2$O$_7$ (M+H)$^+$: 589. Found: 589.

EXAMPLE 10

This example illustrates the preparation of 7-ethylcamptothecin 10,20-di-O-linoleicate (CY201). To a solution of SN38 (279 mg, 0.71 mmol) in pyridine (30 mL) at 0° C. was added linoleic anhydride (2 mL, 4.24 mmol). The reaction mixture was stirred at room temperature for 21 h and quenched by 20 mL of methanol. The mixture was stirred for additional 2 h at room temperature and concentrated on rotavapor to dryness. The residue was purified by flash silica gel column chromatography (THF:DCM, 1:45) to afford a pale yellow solid (283 mg, 43%). $^1$H NMR (CDCl$_3$, 500 MHz): δ 8.29 (d, J=9.2 Hz, 1H), 7.85 (d, J=2.4 Hz, 1H), 7.58 (dd, J=9.2, 2.4 Hz, 1H), 7.31 (s, 1H), 5.68 (d, J=17.2 Hz, 1H), 5.41-5.21 (m, 1H), 3.16 (dd, J=15.2, 7.6 Hz, 2H), 2.78-2.73

(m, 6H), 2.66 (t, J=7.5 Hz, 2H), 2.55-2.46 (m, 2H), 2.35 (t, J=7.5 Hz, 4H), 1.99-1.85 (m, 4H), 1.84-1.78 (m, 4H), 1.66-1.25 (m, 3H), 0.97 (t, J=6.9 Hz, 3H), 0.89-0.85 (m, 6H). ESI-MS: calcd. for $C_{58}H_{81}N_2O_7$ (M+H)$^+$: 918. Found: 918.

EXAMPLE 11

This example illustrates the preparation of 7-ethylcamptothecin 10,20-di-O-decanoicate (CY203). To a solution of SN38 (203 mg, 0.51 mmol) in pyridine (25 mL) at 0° C. was added decanoic anhydride (1.39 g, 4.24 mmol). The reaction mixture was stirred at room temperature for 21 h and quenched by 10 mL of methanol. The mixture was stirred for additional 3 h at room temperature and concentrated on rotavapor to dryness. The residue was purified by flash silica gel column chromatography (THF:DCM, 1:45) to afford a pale yellow solid (292 mg, 81%). $^1$H NMR (CDCl$_3$, 500 MHz): δ 8.22 (d, J=9.1 Hz, 1H, 12-H), 7.82 (d, J=2.5 Hz, 1H, 9-H), 7.56 (dd, J=9.2, 2.4 Hz, 1H, 11-H), 7.19 (s, 1H, 14-H), 5.68 (d, J=17.1 Hz, 1H, 17-H), 5.41 (d, J=17.2 Hz, 1H, 17-H), 5.24 (d, J=3.8 Hz, 2H, 5-H), 3.15 (dd, J=15.4, 7.7 Hz, 2H, C7-methylene), 2.66 (t, J=7.5 Hz, 2H, methylene), 2.35 (t, J=7.5 Hz, 4H, methylene), 1.66-1.25 (m, 3H), 0.97 (t, J=6.8 Hz, 3H, methyl), 0.89-0.85 (m, 6H, methyl). ESI-MS: calcd. for $C_{42}H_{57}N_2O_7$ (M+H)$^+$: 701. Found: 701.

EXAMPLE 12

This example illustrates the preparation of 7-ethylcamptothecin 10,20-di-O-myristate (CY204). To a solution of SN38 (332 mg, 0.85 mmol) in pyridine (25 mL) at 0° C. was added decanoic anhydride (2.24 g, 5.11 mmol). The reaction mixture was stirred at room temperature for 26 h and quenched by 10 mL of methanol. The mixture was stirred for additional 3 h at room temperature and concentrated on rotavapor to dryness. The residue was purified by flash silica gel column chromatography (THF:DCM, 1:45) to afford a white solid (539 mg, 78%). $^1$H NMR (CDCl$_3$, 500 MHz): δ 8.22 (d, J=9.2 Hz, 1H), 7.82 (d, J=2.4 Hz, 1H), 7.56 (dd, J=9.1, 2.4 Hz, 1H), 7.20 (s, 1H), 5.67 (d, J=17.2 Hz, 1H), 5.41 (d, J=17.2 Hz, 1H), 5.25 (d, J=4.0 Hz, 2H), 3.15 (dd, J=15.2, 7.8 Hz, 2H), 2.66 (t, J=7.8 Hz, 2H), 2.33 (t, J=7.5 Hz, 4H), 1.66-1.25 (m, 47H), 0.97 (t, J=6.8 Hz, 3H), 0.89-0.80 (m, 6H). ESI-MS: calcd. for $C_{50}H_{73}N_2O_7$ (M+H)$^+$: 814. Found: 814.

EXAMPLE 13

This example illustrates the preparation of 7-ethylcamptothecin 10,20-di-O-laurate (CY205). To a solution of SN38 (245 mg, 0.63 mmol) in pyridine (30 mL) at 0° C. was added lauric anhydride (1.44 g, 3.76 mmol). The reaction mixture was stirred at room temperature for 24 h and quenched by 10 mL of methanol. The mixture was stirred for additional 3 h at room temperature and concentrated on rotavapor to dryness. The residue was purified by flash silica gel column chromatography (THF:DCM, 1:40) to afford a white solid (388 mg, 82%). $^1$H NMR (CDCl$_3$, 500 MHz): δ 8.22 (d, J=9.1 Hz, 1H), 7.83 (d, J=2.1 Hz, 1H), 7.56 (dd, J=9.1, 2.1 Hz, 1H), 7.19 (s, 1H), 5.68 (d, J=17.2 Hz, 1H), 5.42 (d, J=17.2 Hz, 1H), 5.25 (d, J=4.0 Hz, 2H), 3.15 (dd, J=15.2, 7.8 Hz, 2H), 2.66 (t, J=7.8 Hz, 2H), 2.52-2.48 (m, 2H), 2.33 (t, J=7.5 Hz, 4H), 1.66-1.25 (m, 37H), 0.97 (t, J=6.8 Hz, 3H), 0.89-0.80 (m, 6H). ESI-MS: calcd. for $C_{46}H_{65}N_2O_7$ (M+H)$^+$: 757. Found: 757.

EXAMPLE 14

This example illustrates the preparation of 7-ethylcamptothecin 10,20-di-O-stearate (CY206). To a solution of SN38 (195 mg, 0.50 mmol) in pyridine (40 mL) at 0° C. was added stearic anhydride (1.64 g, 2.98 mmol). The reaction mixture was stirred at room temperature for 48 h and quenched by 10 mL of methanol. The mixture was stirred for additional 5 h at room temperature and concentrated on rotavapor to dryness. The residue was purified by flash silica gel column chromatography (THF:DCM, 1:40) to afford a yellow solid (396 mg, 86%). $^1$H NMR (CDCl$_3$, 500 MHz): δ 8.21 (d, J=9.1 Hz, 1H), 7.82 (d, J=2.2 Hz, 1H), 7.55 (dd, J=9.1, 2.2 Hz, 1H), 7.19 (s, 1H), 5.68 (d, J=17.3 Hz, 1H), 5.41 (d, J=17.3 Hz, 1H), 5.24 (d, J=4.0 Hz, 2H), 3.15 (dd, J=15.2, 7.6 Hz, 2H), 2.66 (t, J=7.6 Hz, 2H), 2.51-2.42 (m, 2H), 2.36 (t, J=7.8 Hz, 4H), 1.68-1.25 (m, 61H), 0.97 (t, J=6.8 Hz, 3H), 0.87-0.80 (m, 6H). ESI-MS: calcd. for $C_{58}H_{89}N_2O_7$ (M+H)$^+$: 926. Found: 926.

EXAMPLE 15

This example illustrates the preparation of 7-ethylcamptothecin 10,20-di-O-(2'-methylheptanoate) (CY212). To a solution of SN38 (300 mg, 0.76 mmol) in pyridine (40 mL) at 0° C. was added 2'-methylheptanoic anhydride (1.24 g, 4.59 mmol). The reaction mixture was stirred at room temperature for 16 h and quenched by 10 mL of methanol. The mixture was stirred for additional 4 h at room temperature and concentrated on rotavapor to dryness. The residue was purified by flash silica gel column chromatography (THF:DCM, 1:30) to afford a yellow solid (400 mg, 81%). $^1$H NMR (CDCl$_3$, 500 MHz): δ 8.20 (dd, J=9.0, 4.1 Hz, 1H), 7.78 (d, J=2.2 Hz, 1H), 7.54 (dd, J=9.1, 2.2 Hz, 1H), 7.20 (d, J=0.8 Hz, 1H), 5.67 (dd, J=17.3, 2.1 Hz, 1H), 5.41 (dd, J=17.3, 2.1 Hz, 1H), 5.25 (d, J=1.7 Hz, 2H), 3.15 (dd, J=15.0, 7.6 Hz, 2H), 2.64-2.59 (m, 2H), 2.47-2.38 (m, 2H), 2.35-2.25 (m, 2H), 1.75-1.25 (m, 23H), 1.08 (t, J=7.4 Hz, 3H), 1.02-0.94 (m, 6H). ESI-MS: calcd. for $C_{38}H_{49}N_2O_7$ (M+H)$^+$: 645. Found: 645.

EXAMPLE 16

This example illustrates the preparation of 7-ethylcamptothecin 10,20-di-O-palmitate (CY213). To a solution of SN38 (246 mg, 0.63 mmol) in pyridine (40 mL) at 0° C. was added palmitic anhydride (1.87 g, 3.78 mmol). The reaction mixture was stirred at room temperature for 24 h and quenched by 10 mL of methanol. The mixture was stirred for additional 4 h at room temperature and concentrated on rotavapor to dryness. The residue was purified by flash silica gel column chromatography (THF:DCM, 1:30) to afford a yellow solid (500 mg, 92%). $^1$H NMR (CDCl$_3$, 500 MHz): δ 8.23 (dd, J=9.2, 4.0 Hz, 1H), 7.82 (d, J=2.2 Hz, 1H), 7.56 (dd, J=9.2, 2.2 Hz, 1H), 7.21 (s, 1H), 5.68 (dd, J=17.2, 2.2 Hz, 1H), 5.42 (dd, J=17.2, 2.1 Hz, 1H), 5.25 (d, J=1.8 Hz, 2H), 3.15 (dd, J=15.0, 7.8 Hz, 2H), 2.66 (t, J=7.5 Hz, 2H), 2.52-2.43 (m, 2H), 2.35 (t, J=7.5 Hz, 3H), 1.85-1.25 (m, 54H), 1.08 (t, J=7.2 Hz, 3H), 0.96-0.86 (m, 6H), ESI-MS: calcd. for $C_{54}H_{81}N_2O_7$ (M+H)$^+$: 870. Found: 870.

EXAMPLE 17

This example showed the in vitro growth inhibition experiments for the compounds in the invention on MX-1 (human breast carcinoma) cells. The cytotoxicity assay was quantitated using the Promega CellTiter Blue Cell Viability Assay. Briefly, cells (5000 cells/well) were plated onto 96-well microtiter plates in RPMI 1640 medium supplemented with 10% FBS and incubated at 378 C in a humidified 5% CO$_2$ atmosphere. After 24 h, cells were exposed to various concentrations of compound in DMSO and cultured for another 72 h. 100 µl of media were removed and 20 µl of Promega CellTiter Blue reagent were added to each well and shaken to mix. After 4 hours of incubation at 37° C. in a humidified 5% $CO_2$ atmosphere, the plates were read at 544 ex/620 em. The fluorescence produced is proportional to the number of viable cells. After plotting fluorescence produced against drug concentration, the $IC_{50}$ was calculated as the half-life of the resulting non-linear regression. The data showed in Table 1.

TABLE 1

$IC_{50}$ of camptothecin analogs.

| | Substitutes | | | $IC_{50}$ |
|---|---|---|---|---|
| ID | $R_4$ | R | MW | μM |
| CY1 | H | $COCH_2CH_2CH_3$ | 504.53 | 151 |
| CY2 | H | $COCH(CH_3)_2$ | 504.53 | 22.8 |
| CY4 | H | $COCH_2CH_2CH_2CH_3$ | 560.64 | 7.8 |
| CY28 | H | $COCH_2NHCOOtBu$ | 678.69 | 221 |
| CY30 | H | $COCH_2OCH_3$ | 508.48 | 372 |
| CY32 | H | $COCH_2NH_2$ | 478.45 | 242 |
| CY55 | H | COPh | 572.56 | 739 |
| CY57 | Et | $COCH_2CH_3$ | 504.54 | 27 |
| CY189 | Et | $CO(CH_2)_4CH_3$ | 588.69 | 3.4 |
| CY201 | Et | $CO(CH_2)_8CH=CHCH=CH(CH_2)_4CH_3$ | 917.26 | 500 |
| CY203 | Et | $CO(CH_2)_8CH_3$ | 700.90 | 2000 |
| CY204 | Et | $CO(CH_2)_{12}CH_3$ | 813.12 | >50* |
| CY205 | Et | $CO(CH_2)_{10}CH_3$ | 757.01 | >50* |
| CY206 | Et | $CO(CH_2)_{16}CH_3$ | 925.33 | >50* |
| CY212 | Et | $CO(CH_2)_3CH(CH_3)CH_2CH_3$ | 644.80 | 294 |
| CY213 | Et | $CO(CH_2)_{14}CH_3$ | 869.22 | >50* |
| 10-HCPT | H | H | 348.35 | 13.5 |
| SN-38 | Et | H | 392.40 | 267 |

Note:
$IC_{50}$ > 50* means the compounds insoluble at higher concentration.

EXAMPLE 18

This example illustrates the preparation of camptothecin 10,20-di-O-hexonate-albumin compositions. 30 mg camptothecin 10,20-di-O-hexonate (as prepared in Example 3) was dissolved in 3.0 mL methylene chloride/methanol (9/1). The solution was then added into 27.0 mL of human serum albumin solution (3% w/v). The mixture was homogenized for 5 minutes at low RPM (Vitris homogenizer model: Tempest I.Q.) in order to form a crude emulsion, and then transferred into a high-pressure homogenizer (Avestin). The emulsification was performed at 9000-40,000 psi while recycling the emulsion for at least 5 cycles. The resulting system was transferred into a Rotavap and solvent was rapidly removed at 40° C., at reduced pressure (30 mm Hg), for 20-30 minutes. The resulting dispersion was translucent and the typical average diameter of the resulting particles was in the range 50-220 nm (Z-average, Malvern Zetasizer). The dispersion was further lyophilized for 48 hours. The resulting cake could be easily reconstituted to the original dispersion by addition of sterile water or saline. The particle size after reconstitution was the same as before lyophilization. It should be recognized that the amounts, types and proportions of drug, solvents, proteins used in this example are not limiting in anyway.

EXAMPLE 19

This example illustrates the formation of nanoparticles of camptothecin di-ester by using cavitation and high shear forces during a sonication process. Thus, 20 mg Camptothecin 10,20-di-O-hexonate (as prepared in Example 3) was dissolved in 1.0 mL methylene chloride. The solution was added to 4.0 mL of human serum abumin solution (5% w/v). The mixture was homogenized for 5 minutes at low RPM (Vitris homogenizer, model: Tempest I.Q.) in order to form a crude emulsion, and then transferred into a 40 kHz sonicator cell. The sonicator was performed at 60-90% power at 0 degrees for 1 min (550 Sonic Dismembrator). The mixture was transferred into a Rotary evaporator, and methylene chloride is rapidly removed at 40° C., at reduced pressure (30 mm Hg), for 20-30 minutes. The typical diameter of the resulting paclitaxel particles was 350-420 nm (Z-average, Malvern Zetasizer).

The dispersion was further lyophilized for 48 h without adding any cryoprotectant. The resulting cake could be easily reconstituted to the original dispersion by addition of sterile water or saline. The particle size after reconstitution was the same as before lyophilization.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A di-ester compound having the following structure:

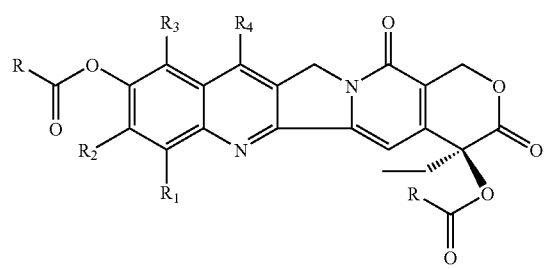

wherein $R_1$, $R_2$, $R_3$, and $R_4$, which can be the same or different, are hydrogen, halogen, $C_1$-$C_{20}$ alkyl, $C_1$-$C_8$ alkoxyl, $C_4$-$C_{20}$ aryl or $C_1$-$C_{20}$ silyl, R, which can be the same or different, is $C_2$-$C_{30}$ alkyl, $C_2$-$C_{22}$ alkenyl, $C_4$-$C_{30}$ aryl, $(CH_2)_nOR_5$, $(CH_2)_nSR_5$, $(CH_2)_nNR_5R_6$ or $(CH_2)_nCOR_7$, $R_5$ and $R_6$, which can be the same or different, are $C_1$-$C_8$ alkyl or $C_2$-$C_6$ alkenyl, $R_7$ is hydroxy, $C_1$-$C_{20}$ alkyl, $C_1$-$C_6$ alkenyl, $C_1$-$C_6$ alkoxy, $C_4$-$C_{20}$ aryl, or $NR_8R_9$, $R_8$ and $R_9$, which can be the same or different, are $C_1$-$C_6$ alkyl, and n is an integer of 1 to 8, or a pharmaceutically acceptable salt thereof.

2. A di-ester compound of claim 1 wherein each R can be the same or different and is $C_2$-$C_{20}$ alkyl, $C_2$-$C_6$ alkenyl or $C_4$-$C_{20}$ aryl.

3. A pharmaceutical composition comprising an effective amount of the di-ester compound of claim 1 and a pharmaceutically acceptable carrier or diluent.

4. A pharmaceutical composition comprising an effective amount of the di-ester compound of claim 2 and a pharmaceutically acceptable carrier or diluent.

5. The di-ester compound of claim 1, wherein each of $R_1$, $R_2$, $R_3$, $R_4$ is H, and R is $C_2$-$C_{30}$ alkyl.

6. The di-ester compound of claim 2, wherein each of $R_1$, $R_2$, $R_3$, $R_4$ is H, and R is $C_2$-$C_{20}$ alkyl.

7. The di-ester compound of claim 1, wherein each of $R_1$, $R_2$, $R_3$, $R_4$ is H, and R is $C_2$-$C_{22}$ alkenyl.

8. The di-ester compound of claim 1, wherein each of $R_1$, $R_2$, $R_3$, and $R_4$ is H, and R is $C_2$-$C_6$ alkenyl.

9. The di-ester compound of claim 1, wherein each of $R_1$, $R_2$, $R_3$ $R_4$ is H, and R is $(CH_2)_nOR_5$, $R_5$ is $C_1$-$C_6$ alkyl or $C_2$-$C_6$ alkenyl, and n is 1 or 2.

10. The di-ester compound of claim 1, wherein each of $R_1$, $R_2$, $R_3$ and $R_4$ is H, and R is $(CH_2)_nSR_5$, $R_5$ is $C_1$-$C_6$ alkyl or $C_2$-$C_6$ alkenyl and n is 1 or 2.

11. The di-ester compound of claim 1, wherein each of $R_1$, $R_2$, $R_3$ $R_4$ is H, and R is $(CH_2)_nNR_5R_6$, $R_5$ and $R_6$ are independently $C_1$-$C_6$ alkyl or $C_2$-$C_6$ alkenyl, and n is 1 or 2.

12. The di-ester compound of claim 1, wherein each of $R_1$, $R_2$, $R_3$ $R_4$ is H, R is $(CH_2)_nCOR_7$ $R_7$, is hydroxy, $C_1$-$C_6$ alkyl, $C_2$-$C_6$ alkenyl or $C_4$-$C_{10}$ aryl, and n is 2 to 4.

13. The di-ester compound of claim 1, wherein each of $R_1$, $R_2$ and $R_3$ is H, $R_4$ is $CH_2CH_3$, and R is $C_2$-$C_{30}$ alkyl.

14. The di-ester compound of claim 2, wherein each of $R_1$, $R_2$ and $R_3$ is H, $R_4$ is $CH_2CH_3$, and R is $C_2$-$C_{20}$ alkyl.

15. The di-ester compound of claim 1, wherein each of $R_1$, $R_2$ and $R_3$ is H, $R_4$ is $CH_2CH_3$, and R is $C_2$-$C_{22}$ alkenyl.

16. The di-ester compound of claim 2, wherein each of $R_1$, $R_2$ and $R_3$ is H, $R_4$ is $CH_2CH_3$, and R is $C_2$-$C_6$ alkenyl.

17. The di-ester compound of claim 1, wherein each of $R_1$, $R_2$ and $R_3$ is H, $R_4$ is $CH_2CH_3$, and R is $C_4$-$C_{30}$ aryl.

18. The di-ester compound of claim 2, wherein each of $R_1$, $R_2$ and $R_3$ is H, R is $CH_2CH_3$, and R is $C_4$-$C_{20}$ aryl.

19. The di-ester compound of claim 1, wherein each of $R_1$, $R_2$ and $R_3$ is H, $R_4$ is $CH_2CH_3$, R is $(CH_2)_nOR_5$, $R_5$ is $C_1$-$C_6$ alkyl or $C_2$-$C_6$ alkenyl, and n is 1 or 2.

20. The di-ester compound of claim 1, wherein each of $R_1$, $R_2$ and $R_3$ is H, $R_4$ is $CH_2CH_3$, and R is $(CH_2)_nSR_5$, $R_5$ is $C_1$-$C_6$ alkyl a $C_2$-$C_6$ alkenyl and n is 1 or 2.

21. The di-ester compound of claim 1 or a salt thereof, wherein each of $R_1$, $R_2$ and $R_3$ is H, $R_4$ is $CH_2CH_3$, and R is $(CH_2)_nNR_5R_6$, $R_5$ and $R_6$ are independently $C_1$-$C_6$ alkyl or $C_2$-$C_6$ alkenyl, and n is 1 or 2.

22. The di-ester compound of claim 1, wherein each of $R_1$, $R_2$ and $R_3$ is H, $R_4$ is $CH_2CH_3$, R is $(CH_2)_nCOR_7$, $R_7$ is hydroxy, $C_1$-$C_6$ alkyl, $C_2$-$C_6$ alkenyl or $C_4$-$C_{10}$ aryl, and n is 2 to 4.

23. The di-ester compound of claim 1, wherein each of $R_1$, $R_2$ and $R_3$ is H, R is $Si(CH_3)_2C(CH_3)_3$, and R is $C_2$-$C_{30}$ alkyl.

24. The di-ester compound of claim 2, wherein each of $R_1$, $R_2$ and $R_3$ is H, $R_4$ is $Si(CH_3)_2C(CH_3)_3$, and R is $C_2$-$C_{20}$ alkyl.

25. The di-ester compound of claim 1, wherein each of $R_1$, $R_2$ and $R_3$ is H, $R_4$ is $Si(CH_3)_2C(CH_3)_3$, and R is $C_2$-$C_{22}$ alkenyl.

26. The di-ester compound of claim 2, wherein each of $R_1$, $R_2$ and $R_3$ is H, $R_4$ is $Si(CH_3)_2C(CH_3)_3$, and R is $C_2$-$C_6$ alkenyl.

27. The di-ester compound of claim 1, wherein each of $R_1$, $R_2$ and $R_3$ is H, $R_4$ is $Si(CH_3)_2C(CH_3)_3$, and R is $C_4$-$C_{30}$ aryl.

28. The di-ester compound of claim 2, wherein each of $R_1$, $R_2$ and $R_3$ is H, $R_4$ is $Si(CH_3)_2C(CH_3)_3$, and R is $C_4$-$C_{20}$ aryl.

29. The di-ester compound of claim 1, wherein each of $R_1$, $R_2$ and $R_3$ is H, $R_4$ is $Si(CH_3)_2C(CH_3)_3$, R is $(CH_2)_nOR_5$, $R_5$ is $C_1$-$C_6$ alkyl or $C_2$-$C_6$ alkenyl, and n is 1 or 2.

30. The di-ester compound of claim 1, wherein each of $R_1$, $R_2$ and $R_3$ is H, $R_4$ is $Si(CH_3)_2C(CH_3)_3$, and R is $(CH_2)_nSR_5$, $R_5$ is $C_1$-$C_6$ alkyl or $C_2$-$C_6$ alkenyl and n is 1 or 2.

31. The di-ester compound of claim 1 or a salt thereof, wherein each of $R_1$, $R_2$ and $R_3$ is H, $R_4$ is $Si(CH_3)_2C(CH_3)_3$, R is $(CH_2)_nNR_5R_6$, $R_5$ and $R_6$ are independently, $C_1$-$C_6$ alkyl or $C_2$-$C_6$ alkenyl, and n is 1 or 2.

32. The di-ester compound of claim 1, wherein each of $R_1$, $R_2$ and $R_3$ is H, $R_4$ is $Si(CH_3)_2C(CH_3)_3$, R is $(CH_2)_nCOR_7$, $R_7$ is hydroxy, $C_1$-$C_6$ alkyl, $C_2$-$C_6$ alkenyl or $C_4$-$C_{10}$ aryl, and n is 2 to 4.

33. The di-ester compound of claim 1, wherein $R_1$ is $CH_2N(CH_3)_2$, each of $R_2$, $R_3$ and $R_4$ is H, and R is $C_2$-$C_{30}$ alkyl.

34. The di-ester compound of claim 2, wherein $R_1$ is $CH_2N(CH_3)_2$, each of $R_2$, $R_3$ and $R_4$ is H, and R is $C_2$-$C_{20}$ alkyl.

35. The di-ester compound of claim 1, wherein $R_1$ is $CH_2N(CH_3)_2$, each of $R_2$, $R_3$ and $R_4$ is H, and R is $C_2$-$C_{22}$ alkenyl.

36. The di-ester compound of claim 2, wherein $R_1$ is $CH_2N(CH_3)_2$, each of $R_2$, $R_3$ and $R_4$ is H, and R is $C_2$-$C_6$ alkenyl.

37. The di-ester compound of claim 1, wherein $R_1$ is $CH_2N(CH_3)_2$, each of $R_2$, $R_3$ and $R_4$ is H, and R is $C_4$-$C_{30}$ aryl.

38. The di-ester compound of claim 2, wherein $R_1$ is $CH_2N(CH_3)_2$, each of $R_2$, $R_3$ and $R_4$ is H, and R is $C_4$-$C_{20}$ aryl.

39. The di-ester compound of claim 1, wherein $R_1$ is $CH_2N(CH_3)_2$, each of $R_2$, $R_3$ and $R_4$ is H, R is $(CH_2)_nOR_5$, $R_5$ is $C_1$-$C_6$ alkyl or $C_2$-$C_6$ alkenyl, and n is 1 or 2.

40. The di-ester compound of claim 1, wherein $R_1$ is $CH_2N(CH_3)_2$, each of $R_2$, $R_3$ and $R_4$ is H, and R is $(CH_2)_nSR_5$, $R_5$ is $C_1$-$C_6$ alkyl or alkenyl and n is 1 or 2.

41. The di-ester compound of claim 1, wherein $R_1$ is $CH_2N(CH_3)_2$, each of $R_2$, $R_3$ and $R_4$ is H, R is $(CH_2)_nNR_5R_6$, $R_5$ and $R_6$ are independently, $C_1$-$C_6$ alkyl or $C_2$-$C_6$ alkenyl, and n is 1 or 2.

42. The di-ester compound of claim 1, wherein $R_1$ is $CH_2N(CH_3)_2$, each of $R_2$, $R_3$ $R_4$ is H, and R is $(CH_2)_nCOR_7$, $R_7$ is hydroxy, $C_1$-$C_6$ alkyl, $C_2$-$C_6$ alkenyl or $C_4$-$C_{10}$ aryl, and n is 2 to 4.

43. A method to inhibit the enzyme topoisomerase I in an animal in need thereof comprising administering to the animal an effective amount of a composition comprising at least one di-ester compound of claim 1.

44. A method to inhibit the enzyme topoisomerase I in an animal in need thereof comprising administering to the animal an effective amount of a composition comprising at least one di-ester compound of claim 2.

45. A method to treat cancer in a patient comprising administering a composition comprising at least one di-ester compound of claim 1 to said patient in an amount effective to treat said cancer.

46. A method to treat cancer in a patient comprising administering a composition comprising at least one di-ester compound of claim 2 to said patient in an amount effective to treat said cancer.

47. The method of claim 45, wherein said cancer is lung, breast, colon, prostate, melanoma, pancreas, stomach, liver, brain, kidney, uterus, cervix, ovaries, urinary tract, gastrointestinal, or leukemia.

48. The method of claim 46, wherein said cancer is lung, breast, colon, prostate, melanoma, pancreas, stomach, liver, brain, kidney, uterus, cervix, ovaries, urinary tract, gastrointestinal, or leukemia.

49. The method of claim 45, wherein said cancer is solid tumor or blood borne tumor.

50. The method of claim 46, wherein said cancer is solid tumor or blood borne tumor.

51. The method of claim 45, wherein said composition is administered orally, parenterally, intramuscularly, transdermally or by an airborne delivery system.

52. The method of claim 46, wherein said composition is administered orally, parenterally, intramuscularly, transdermally or by an airborne delivery system.

53. The method of claim 45, wherein said composition is a nanoparticle containing said at least one di-ester compound.

54. The method of claim 46, wherein said composition is a nanoparticle containing said at least one di-ester compound.

55. A method to treat breast cancer in a patient comprising administering a composition comprising at least one di-ester compound of claim 1 to said patient in an amount effective to treat said cancer.

56. A method to treat breast cancer in a patient comprising administering a composition comprising at least one di-ester compound of claim 2 to said patient in an amount effective to treat said cancer.

* * * * *